United States Patent [19]

Wentworth et al.

[11] Patent Number: 5,317,271

[45] Date of Patent: May 31, 1994

[54] HIGH VOLTAGE SPARK EXCITATION AND IONIZATION DETECTOR SYSTEM WITH ADJUSTABLE SAMPLE INPUT FOR SENSITIVITY CONTROL

[75] Inventors: Wayne E. Wentworth; Stanley D. Stearns, both of Houston, Tex.

[73] Assignee: Valco Instruments, Co., Houston, Tex.

[21] Appl. No.: 956,632

[22] Filed: Oct. 5, 1992

Related U.S. Application Data

[63] Continuation-in-part of Ser. No. 662,149, Mar. 28, 1991, Pat. No. 5,153,519.

[51] Int. Cl.$^5$ .................. G01N 27/62; G01N 27/68
[52] U.S. Cl. .................. 324/464; 324/455; 73/28.02
[58] Field of Search ............ 324/123 R, 71, 21, 449, 324/450, 452, 455, 464; 73/28.02; 436/153; 313/231.41, 231.71; 315/111.01, 111.91; 250/379, 385.2

[56] References Cited

U.S. PATENT DOCUMENTS

| | | |
|---|---|---|
| 3,238,367 | 3/1966 | Sternberg . |
| 3,378,725 | 4/1968 | Bochinski et al. . |
| 3,418,514 | 12/1968 | Sternberg . |
| 3,446,964 | 5/1969 | Sternberg . |
| 3,540,851 | 11/1970 | Vree et al. . |
| 4,780,284 | 10/1988 | Lovelock . |
| 4,851,683 | 7/1989 | Yang et al. . |
| 4,866,278 | 9/1989 | Lovelock . |
| 5,153,519 | 10/1992 | Wentworth et al. ............ 324/449 |

FOREIGN PATENT DOCUMENTS

| | | |
|---|---|---|
| 0184912 | 6/1986 | European Pat. Off. . |
| 0396291 | 11/1990 | European Pat. Off. . |

OTHER PUBLICATIONS

Sternberg et al, "A Tesla Discharge Detector for Gas Chromatography", Mar. 1960, pp. 406–410.
Rosick et al., "Analytical Parameters of a Photoionization Detector for Gas Chromatography", 1976, pp .1251–1259.
P. L. Patterson, "Mobilities of Polyatomic Ions", The Journal of Chemical Physics, vol. 56, No. 8, Apr. 15, 1972, pp. 3943–3947.
P. L. Patterson, "Temperature Dependence of Helium-Ion Mobilities", Physical Review, vol. 2, No. 4, Oct. 1970, pp. 1154–1164.
Wentworth et al, "Photo-electron Capture Detector", Journal of Chromatography, 112 (1975), pp. 229–246.
P. L. Patterson, "Evidence of the Existence of an $He_3^+$ Ion*", the Journal of Chemical Physics, vol. 48, No. 8, Apr. 1968, pp. 3625–3631.
Beaty et al, "Mobilities and Reaction Rates of Ions in Helium", the Physical Review, vol. 137, No. 2A, Jan. 18, 1965, pp. A346–A357.
P. L. Patterson, "Mobilities of Negative Ions in $SF_6$", the Journal of Chemical Physics, vol. 53, No. 2, Jul. 15, 1970, pp. 696–704.
Bundi et al, "Mobilities of Atomic and Molecular Ions in the Noble Gases", Physical Review, vol. 94, No. 4, May 15, 1954, pp. 910–916.

*Primary Examiner*—Gerard R. Strecker
*Assistant Examiner*—Diep Do
*Attorney, Agent, or Firm*—Donald Gunn

[57] ABSTRACT

A sample is loaded along with a carrier gas into a column. The column discharge is introduced into a chamber downstream of spaced electrodes which create a pulsed DC spark. The spark produces a spectral emission and a metastable carrier gas dispersion that then reacts with molecules of the sample to bring the sample to an excited state. The excess energy surrendered by the sample is characteristic of the species and can be measured by detector electrodes in the chamber.

25 Claims, 3 Drawing Sheets

HIGH VOLTAGE SPARK EXCITATION AND IONIZATION DETECTOR SYSTEM WITH ADJUSTABLE SAMPLE INPUT FOR SENSITIVITY CONTROL

BACKGROUND OF THE DISCLOSURE

This disclosure is a continuation in part of application Ser. No. 662,149 which was filed on Feb. 28, 1991 and which issued as U.S. Pat. No. 5,153,519 on Oct. 6, 1992.

The present disclosure involves the creation of several charged species by a pulsed DC spark discharge acting on a carrier gas, typically helium, which utilizes the charged species to classify and/or quantify compounds in the carrier. This detector is connected with upstream or downstream devices such as a sample source, gas chromatography (GC) column spectrum analyzers, etc. Understanding of various test procedures will illuminate use of the described apparatus and can be gained from review of the apparatus and its mode of operation in a system. A sample to be evaluated is first loaded along with a carrier gas into a system column. The sample passes through this device, a pulsed, high voltage discharge, and several types of detection systems are initiated by this detector. For instance, the very short DC spark creates a readily available thermalized electron flux which can be used in a detection system. In an alternate mode of operation, the spark also creates a more slowly diffused flux of metastable helium atoms which drift toward selected electrodes at a controlled rate. The helium atoms will react with molecules of the sample to surrender the excess energy from the excited state to cause sample molecule ionization which, as a secondary reaction, can be measured by a detection system. Another aspect involves transitory photo ionization of a gas into positive and negative charged particles normally recombining at high speed. If a selected sweep pulse voltage is applied, the recombination is prevented to furnish a current signal indicative of gas contents.

The preferred form of this system features a pulsed DC spark discharge in the carrier gas flow which is followed by a rather slow metastable carrier gas dispersion and secondary reaction, which is slow in contrast with the practically instantaneous electron initiated interaction. The DC spark discharge therefore enables two different detection mechanisms, as will be explained, so that variations in detection electrode geometry and pulse timing can obtain different types of responses. One system uses the highly mobile electron flux while an alternate system relies on the metastable carrier gas molecular energy interchange occurring well after the electron flux.

In addition to the particle interaction initiated in the spark manifest in two different aspects, there are also two spectral emissions created by the DC spark, one occurring during the spark and the other occurring later. In the spark gap, the electron discharge creates a first observable spectrum which can be observed by viewing the spark region. Geometry of the spark is sharply defined, narrowly confined, and repetitively located for observation and spectral analysis. This analysis enables detection of the atomic species in the gap. While this first spectrum is extinguished at the end of the spark, a second spectral analysis is enabled by the subsequent decay of the metastable helium atoms giving up their excess energy by ionizing molecules of the sample. This interchange occurs as the energized helium atoms diffuse from the spark gap in the test chamber and with the sample molecules. Dependent on relative concentrations, diffusion and flow rates, the sample molecules are ionized to emit energy characteristics of the species. This delayed emission is useful in species identification when timely observed, and therefore a different mode of observation is used to capture data from its emission. This difference in operation derives primarily from delayed occurrence and observed at a different time.

The present invention uses to advantage a simple spark gap having a pair of spaced electrodes connected to a current pulse forming system. The pulses are extremely narrow, preferably in the range of a fraction of a microsecond. The DC pulses repetitively form precise, sharp and well defined transgap pulses, liberating the electron flux mentioned and also forming the metastable helium molecules. The spark is fixed in size and relative timing, shape and location. Electrode geometry does not erode with time and electron ejection is uniform. Thus, the spark is fixed for observation by spectral analysis. Structurally, this enables a very simple chamber to deploy a pair of opposing, spaced electrodes in a cavity of perhaps 10 to 100 microliters volume with gas flow inlet and outlet ports. In a representative system, a chemical sample is mixed with a carrier gas. The sample is prepared for testing by classification, identification or quantification using the detector. An exemplary system achieves separation as a result of differences in travel time through a GC column input to the detector. As is well known, the GC column is either a wall coated open capillary or packed with a stationary phase material so that the carrier gas and the compounds making up the sample are eluted from the GC column. As a generalization, the mobile phase (a flowing gas or liquid) is delivered by the GC column into this detector for detection of the separated chemical constituents making up the sample.

The detector is operated periodically to test each of the sample constituent compounds passing through the detector. One type of detector used in the past has been the electron capture detector (ECD). The present disclosure sets out an alternate form of ECD detector used in conjunction with a GC column which forms an output signal of substantial sensitivity. The present system features an ECD with a DC pulsed, high voltage spark discharge. As noted at column 2 of U.S. Pat. No. 4,851,683, DC discharges have been known, but they generally have had inhomogeneous excitation characteristics and are unstable because of electrode heating and erosion. U.S. Pat. No. 4,509,855 is a DC atmospheric pressure helium plasma emission spectrometer. Additional devices are shown in U.S. Pat. No. 4,866,278. The present apparatus sets forth a DC pulsed, high voltage, spark discharge source which provides a repetitive uniform spark. The spark has a duration which is only a fraction of a microsecond. It would appear that an acceptable spark duration is a fraction of a microsecond. Moreover, the spark gap is structurally fixed to have a finite width for discharge of the spark created by accumulating energy in a reactive circuit such as a coil and capacitor charging. Preferably, a non-ringing current is applied.

This detector in a representative form includes a means for forming a stabilized spark gap so that the spark and resultant charged particle population are uniform in contrast with the problems referenced in the two mentioned patents. Accordingly, the carrier fluid (e.g., carrier flow from the GC column) is directed as a gas flow through appropriate tubing into a spark chamber. The gas is forced to flow in the spark chamber past a pair of electrodes which are arranged to direct the spark transverse to the gas flow. In a first mode of operation, a flux of electrons is obtained. These electrons are quickly dissipated during the spark interval even though spark duration is only a fraction of a microsecond. The number of electrons available can be measured by means of an electrometer connected to electrodes spaced remotely from the spark gap. The electrometer circuitry connected with a terminal in the chamber and spaced from the spark gap detects and measures the electron flux resulting from the spark discharge. In this instance, the spark gas works as an ECD. There is, however, an alternate charged particle flux which is delayed after the spark discharge which uses an ionization mode. This involves a delay of up to about 100 or even 200 microseconds after the spark discharge creates ionized molecules which are dispersed at a slower rate compared with the more mobile electron dispersal. The spark disperses highly energized electrons during the spark and also creates a second and slower dispersion of metastable carrier gas molecules (preferably helium) after the spark. Charged particle dispersal of the first form is, as a practical matter, instantaneous while metastable helium dispersal is time delayed. The two types of dispersion are readily identified because they involve different types of particles. The dispersal of metastable helium atoms, with an elevated energy state of about twenty or more eV, can be observed at a distance from the spark gap so that sample compound concentration (a scale factor) in the chamber is measured. The metastable helium concentration is useful because it enables this delayed reaction. Thus, the metastable helium atom reacts with the sample molecules input with the carrier flow. The high energy in the helium ionizes the sample molecules, creating a measurable current in the chamber.

Building on the last possibility, metastable helium molecules may combine with a trace constituent such as a dopant supplied with the carrier (helium) gas. One such dopant is nitrogen which, in reaction with the metastable helium, forms nitrogen ions. That causes liberation of electrons which again, because of different mobility, dissipate more readily. Before the electrons recombine with the ionized nitrogen molecules, they will react with the compounds making up the sample flowing through the detector. A connected electrode and electrometer will measure electron capture from the dopant involvement to define an electron capture detector.

Another alternate form of apparatus involves observation of the spectrum emitted in the spark gap. This involves the conversion of the constituents to elevated energy states where emissions occur at characteristic frequencies, and such frequencies can be observed and measured. This typically involves a spectrum analyzer such as a spectrometer which observes one or more atomic or molecular emission lines in selected regions of the spectrum. Spectral line observation varies with the time and location relative to the spark discharge. Regarding time, the observed spectrum is different during and after the spark discharge. Regarding location, the reaction is different in the spark or elsewhere in the chamber. The present apparatus is therefore summarized as a pulsed DC spark discharge where the spark discharge reacts with a carrier gas (preferably helium) and compounds from a sample. In this spark, charged particles are created, the particles being either disassociated electrons, an ionized carrier gas, ionized dopant gas, or highly energized helium atoms in a metastable form. Depending on the timing of measurements, the particular ionized particles and measurement voltages applied, the device can be operated in an ionization mode, or electron capture mode. Molecules of a compound separated by chromatographic separation or other input devices can be quantified. The device also emits characteristic spectral lines depending on the nature and timing of the emission. Moreover, by selection of the carrier gas, the addition of a selected dopant with the gas flow, control of pulsing of the spark gap forming the charged particles, timed operation of measurement electrodes nearby, and adjustment of scale factors, it is possible to operate in several modes. In addition to this, precisely defined spectral lines can be observed.

The present apparatus additionally includes simplified versions of the pulse discharge mechanism cooperative with a GC system. In one instance, the helium metastable molecule is used to achieve ionization of the eluate from the GC column without forcing the eluate to flow through the spark gap. This enhances operation of the equipment because the spark gap region deals primarily in helium, but is protected from contamination by the solvent or the eluate sample flowing from the GC column. In this version of equipment, the GC column discharge is delivered into the chamber at a location where it is not required to flow through the spark gap. As a second alternative, a dopant gas is also added in the flow downstream from the spark gap. It can be added upstream from the delivery of the elute from the GC column. By this approach, it is possible to provide the dopant without forcing it to flow through the spark gap. Again, that reduces contamination of the terminals or electrodes at the spark gap. Further, this type arrangement enables the system to operate as a simple ionization detector. Alternately, it can be operated as an electron capture detector (ECD hereafter). Details of these structures will be given later. Another aspect of the present apparatus is the use of the device to form an emission spectra which provides spectra from various samples through a transparent window. In this aspect of the system, it is provided with a transparent window sealed at the entrance of a monochromator. At this aspect of the invention, the direction of the helium gas flow plus the eluate from the GC column is away from the transparent window so that the reaction products do not contaminate the window which loses transparency as a result of contamination. So to speak, the window is located upstream of the mixing point. Through the use of this mechanism, spectral emissions can be obtained to analyze the constituent components of a sample. For instance, characteristic atomic, ionic, or molecular spectra lines can be classified. One characteristic of the atomic spectra is formation of extremely narrow emission lines with little or no interference between spectra from other atoms or molecules. This is especially helpful in the vacuum ultraviolet region. By contrast, the ultraviolet and visible regions of the spectra may receive broad interfering spectra from many common elements or molecules. Accordingly, it is especially desirable to operate in the vacuum ultraviolet region and in particular the region of about 120–200 nanometers.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENT

The present disclosure is directed to an ionization detector system connected with upstream and downstream equipment. The cooperative equipment defines one context for ease of explanation so that a thorough discussion of the spark detector system will provide the necessary explanation. This is a detector system devoid of radioactive apparatus and hence can be used in circumstances where radioactive materials are limited. Heretofore, it has been common to operate electron capture devices with radioactive sources, the most common sources being tritium or nickel 63. Typically, these emit beta particles which trigger operation of the electron capture detector or perhaps helium ionization detectors. In this particular instance, a non-radioactive device is thereby provided. Going now to FIG. 1 of the drawings, the numeral 20 identifies a detector system of the present disclosure. It will be described proceeding from the input in the fashion of a flow chart, and after that, certain features of the high voltage DC powered pulsed spark discharge system will be discussed, and its interaction with various types of detector system including charge measuring devices and spectrum analyzers will also be set forth. Certain equations will be given which are believed to correctly describe the nature of the particles of the process. At this stage, the detector will be described solely with a carrier gas, and its operation dates will be given with various inputs.

Figure 1:
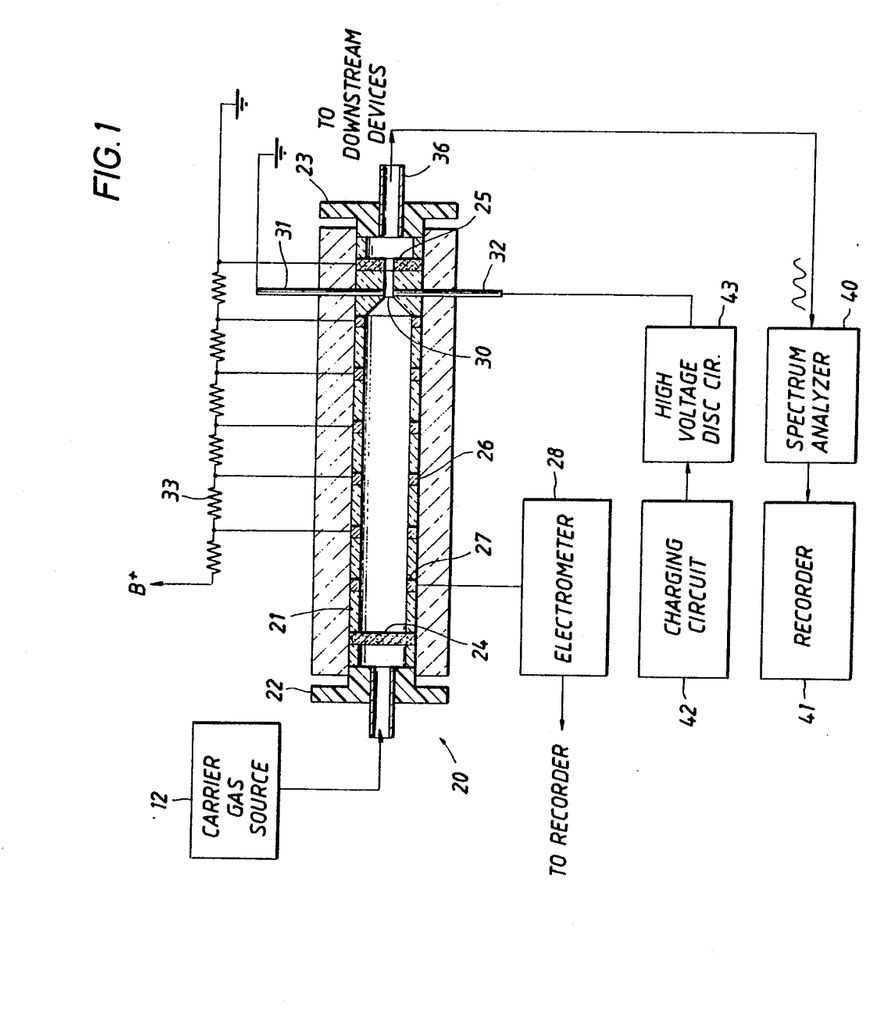
FIG. 1 is schematic block diagram of the detector of this disclosure showing a pair of fixed electrodes in a spark gap for pulsed DC discharge in a flowing stream to form charged particles.

The present detection system utilizes a carrier gas source 12 connected to the detector with an input valve (not shown). The source provides a carrier gas flow and a sample will be discussed later; there is a constant flow delivered into and through the detector at a controlled pressure and flow rate. Briefly, a carrier gas is supplied in a steady flow rate and pressure. Representative sample compounds may include various and sundry halocarbons and other organics which are carried with the flowing carrier gas. For representative purposes, a specimen of the sample will be denoted very generally as the compound AB, it being understood that the strength or concentration of this is variable. The detector 20 of the present disclosure is able to quantify the compound AB even measuring parts per million, and in some instances parts per billion, and in other instances even smaller concentrations. It is preferable that the sample AB be delivered with helium as the carrier gas. While several gases can be used, the preferred carrier gas is helium. Purity will be discussed below. The gas flow is directed to an inlet opening 18 of the plasma detector 20. The detector includes a closed elongate tube 21 which has an end cap 22 opposite a similar end cap 23. They are both provided with ports for flow through the detector. The central tube is axially hollow and has a uniform diameter throughout the length except at the spark electrodes as will be mentioned.

The detector 20 is formed of an insulating material. The tube can be glass or the like. The flow is through transverse disc 24 formed of sintered metal to provide a serpentine inlet pathway and also provide a barrier to charged particle migration further to the left. At spaced locations, there are exposed metal rings such as the ring 25. One of the rings is more remote while other rings are serially closer. The rings are serially arranged downstream from the inlet end. There are several intermediate rings 26 which are tied to various resistors for voltage taps while the ring 25 is illustrated with a ground connection. There is also a ring 27 which is connected to an electrometer 28. The electrometer can be connected elsewhere along the length of the passage; it responds to charged particle population within the tube to detect current flow resulting from charged particle migration.

The number 30 identifies a spark gap which is defined by two round and equal diameter rods. They have a finite width typically in the range of a fraction of a millimeter up to about two millimeters. It is desirable that the two tips are sharpened to points to obtain a very narrow spark width and one which is precisely located. The two tips are held by a support ring which can be integral with the support structure. The two tips are aligned opposite one another so that they are precisely diametrically opposite each other within the passage and thus define the spark gap 30. They are supported by a surrounding structure of nonconductive material such as plastic, ceramic or the like. All flowing gases must pass between the two tips. This passage is ideally a small diameter passage, perhaps having a diameter of about one millimeter, and it can be less; the two electrodes are preferably spaced from one another by something between 0.5 and 1.5 millimeters. They can be spaced slightly farther apart if desired. The two electrode tips are flush and do not protrude into the cylindrical passage.

The two electrodes are identified by the numerals 31 and 32, and the electrode 31 is grounded. The electrode 32 is provided with a high voltage pulse as will be described. A very short pulse is preferred. The caps 22 and 23 at the two ends of the structure seal against the intrusion of external air so that the only gases flowing through the system are the carrier gas and the compound AB mixed with the carrier gas and which interact with the spark as individual compounds pass through the spark discharge.

The several electrodes 26 are connected to a voltage ladder which is made up of several series connected resistors 33. B+ is provided for this system. It can be pulsed off and on, being furnished by a B+ supply 34 subject to control of the timer 16. The voltage can be positive or negative depending on charged particle detection. Moreover, the voltage applied to the rings is proportioned by the resistors 33. To this end, one end of the resistor ladder is grounded and the opposite end is connected at B+, and that voltage is switched off and on as will be described in a timed fashion relative to the pulse formed between the electrodes 31 and 32. The flowing carrier gas including the compound AB is directed through the DC spark generator 20 and flows through the outlet port 36. The port 36 is aligned with the port 18 at the opposite end, and the port 36 is particularly directed at the spark gap 30 between the two electrodes. This serves as an observation port to enable optical inspection of the gap during the spark. This enables photons of light emitted by the spark gap to impinge on an external spectrum analyzer 40 which is positioned opposite the outlet opening 36. In turn, the analyzer connects with a recorder 41 for recording the data as a function of time. The system also includes a charging circuit 43 to provide a timed pulse for firing, that is, a pulse which is timed to initiate formation of various charged particles where representative particle reactions will be detailed later.

Figure 3:
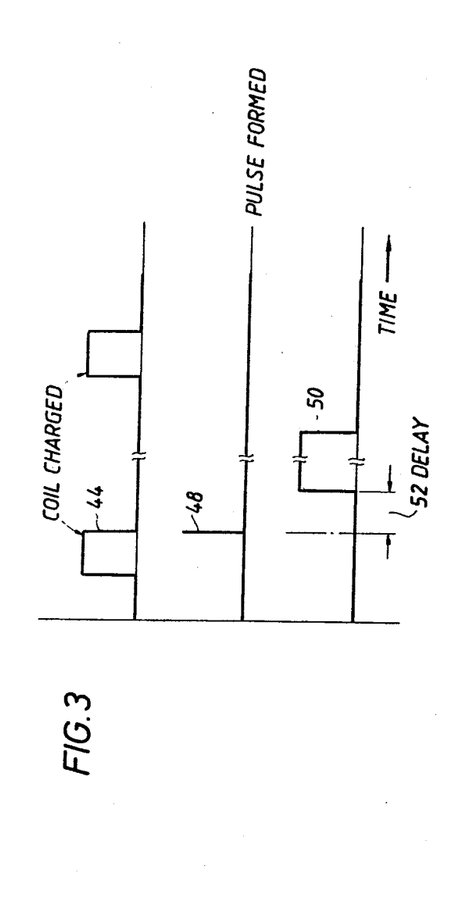
FIG. 3 is a timing chart showing the timed relationship of operations of circuitry shown in FIG. 2 of the drawings.

Going now to FIG. 3 of the drawings, several curves are shown which are a function of time. The top curve shows a charging current in the pulse 44. It forms the necessary charge for operation of the high voltage discharge circuit 43. That circuit forms an output 48 which pulse flows for a relatively short instant. There is a detection interval which is delayed by a specified time 52, and then a detection pulse is formed at 50. Representative values of the pulse duration and spacing will be given.

The spark discharge generator 20 is sealed to exclude external air. It therefore is exposed to a flow of AB and helium in the preferred embodiment. A trace element dopant may optionally be mixed with the carrier gas. A suitable dopant material is $N_2$ which is provided in a controlled quantity, such as one to one thousand parts per million. A typical range for this dopant can be from one part in $10^3$ to one part in $10^9$. The compound AB flows with the carrier helium gas into the chamber and ultimately into the spark gap 30 where the charged particles are formed. The pulse 44 is created for an interval to form the discharge pulse 48. The high voltage discharge circuit 43 forms the discharge pulse 48 which sparks across the gap between the electrodes 31 and 32. Carrier gas in the region of the spark gap 30 is ionized during the spark. The spark is furnished with current flow at a finite voltage; the spark cannot fluctuate because the only mode of current flow is by means of a spark across the gap. The voltage necessary to achieve spark current flow is a function primarily of spacing and tip geometry. The electrode tips are preferably fixed at a known distance from one another so that the voltage necessary to create the spark is fairly stable. Moreover, ambient pressure is maintained in the spark generator 20 so that the voltage does not vary with prevailing pressure. The charging circuit functions like a classic automobile ignition system in that a charging current is provided from a capacitor or the field of a coil and current then collapses to provide the discharge. When the current flows, resistance breaks to the value required to initiate current flow and current flow then drops the collected electrical charge. Preferably, ringing in the supply circuit is suppressed. Moreover, the discharge occurs near the trailing end of the pulse 44 so that the pulse 44 can be used to indicate the time of discharge. It should be noted that the pulse 44 can have a substantial width, ranging from a few microseconds up to many microseconds, at most perhaps 100 to 200 microseconds. Peak amplitude of the discharge pulse 48 is substantially determined by the geometry and spacing of the electrodes 31 and 32.

When current flows through the gap between electrodes 31 and 32, particle excitation occurs. Among other things, elemental helium atoms will be energized when raised to the metastable helium and ultimately diffuses from the spark gap in the chamber in a fashion to be described. While a metastable helium may have an elevated energy level of about twenty eV, it has a fairly long half life, but because of its size, relatively speaking, it diffuses somewhat slowly. The metastable helium atoms will diffuse at some rate in all possible directions. This diffusion rate and range can be enhanced depending on housing geometry and detector electrode geometry, placement and voltage. Moreover, when the pulse occurs, there is a substantial electron discharge into the carrier gas atmosphere from the gap, and is quite high. That is, an extraordinary number of electrons are emitted from and distributed into the immediate atmosphere. These electrons can be observed throughout the generator 20 and can be measured by the electrometer 28 output.

There are several equations which are helpful to describe the relatively simple sequence of events occurring in the plasma tube. Recall again that flow is in that direction, diffusion of the charged particles to the left of the spark gap 30 can be initiated and controlled by choice of polarity and potential on the detector electrodes. Indeed, the mobility of electrons is substantially instantaneous to the extent that electrometer response can be observed rapidly even though the spark has a width of less than one microsecond, perhaps a width of only 10 to 259 nanoseconds. The nearly instantaneous diffusion of electrons primarily results from their extreme mobility in comparison with larger charged particles, namely, the metastable helium. Regarding the spark, the voltage across the terminals is typically several thousand volts prior to current flow; once current flow beings, the voltage across the terminals rapidly changes as current flow changes from the initial zero value toward the peak current and then decays. The pulse duration is relatively easy to define at the start of the pulse but it may be difficult to define at the end of the pulse. There are two reasons for this; the first reason is that the power supply may ring and provide post pulse current reversals. This is preferably suppressed by incorporating means to damp the ringing. A second reason is more subtle, and relates to the ionized particles between the electrodes at the end of the pulse. The resistance across the electrodes may be very low, perhaps so small that it permits current ionized particles between the electrodes are so instantaneously dynamic that current flow can be observed at the facing electrodes even though the power supply, at that instant, provides no voltage.

Figure 2:
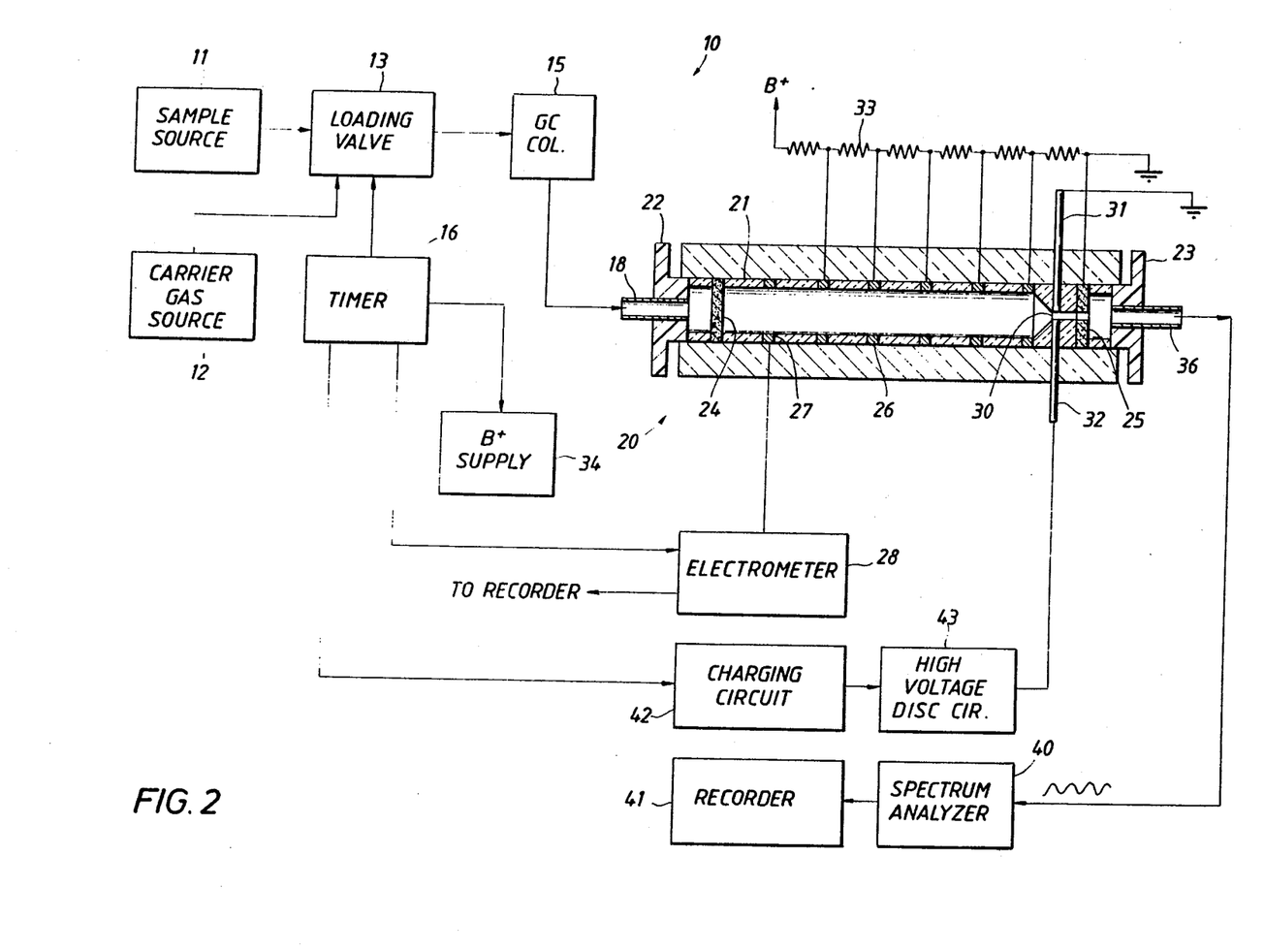
FIG. 2 is a schematic block diagram of a system for testing an unknown sample where the sample and a carrier gas are input through a GC column and the eluate therefrom is directed into a discharge tube having a number of electrodes for charged particle capture and also having a pair of fixed electrodes for pulsed DC discharge in the flowing stream, and further including a spectrum analyzer observing the light emitted on spark discharge.

FIG. 2, shows the present detector in a representative GC system which utilizes a sample source 11 and a carrier gas source 12 which are both connected with a loading valve 13. They provide a carrier gas flow at a constant flow delivered at a controlled pressure and flow rate to a GC column 15. There is a system timer 16 which controls the operation of certain components as will be set forth. Briefly, a carrier gas is supplied in a steady flow for the GC column. Representative compounds include various and sundry halocarbons and other organics which are supplied with the flowing carrier gas through the loading valve 13 to the GC column 15. As before, a specimen of the sample will be denoted very generally as the compound AB, it being understood that the strength or concentration of this is variable. The detector 20 of the present disclosure is able to quantify the compound AB even measuring parts per million, and in some instances parts per billion, and in other instances even smaller concentrations. The discharge of the GC column 15 is directed to an inlet opening 18 of the plasma detector 20.

DESCRIPTION OF CHARGED PARTICLES AND THEIR REACTIONS

There are several results which occur as a result of the spark discharge through the spark gap. For one, the pulsed spark discharge causes immediate energization of molecules (atoms of helium) in the elute. The mechanism apparently involves collision of the high energy electrons in the spark gap with the carrier molecules. In addition to that, molecules (again atoms of helium) in the elute may subsequently emit radiation in a unique spectral distribution characteristic of the excited species and hence form characteristic emission spectra. The several processes occurring during the spark discharge can be summarized by the following five different reactions:

$$e^- + AB \rightarrow AB^+ + e^- \quad (1)$$

$$e^- + AB \rightarrow A + B^+ + e^- \quad (2)$$

$$e^- + AB \rightarrow AB^* + e^- \quad (3)$$

where $AB^* \rightarrow AB + h\gamma$ $$e^- + AB \rightarrow A + B^* + e^- \quad (4)$$

where $B^* \rightarrow B + h\gamma$ $$e^- + AB \rightarrow (AB^+)^* + e^- \quad (5)$$

where $(AB^+)^* \rightarrow AB^+ + h\gamma$

Another reaction which does not occur as a result of the pulsed high voltage spark discharge is the conversion of helium into high energy metastable atoms having an energy of about nineteen eV. This reaction is given in Equation 6:

$$e^- + He \rightarrow He^* + e^- \quad (6)$$

In the foregoing He* represents the metastable helium atom just as the * above in Equations 3, 4 and 5 represents an enhanced energy level for the particular molecule represented by the symbol AB. In the case of metastable helium, it has a relatively long life, depending on the pressure, and the enhanced energy state has sufficient energy to cause subsequent reactions. Equations 7, 8, 9 and 10 describe selected reactions which can occur involving the metastable helium. As will be understood, the metastable helium extends the duration of the process long after the spark discharge is terminated. In fact, the metastable duration can be hundreds of milliseconds while the spark duration might be only a few nanoseconds. The equations below describe various ionization or excitation results from the metastable helium which results are quite different from those initially caused by the high voltage spark discharge set forth in Equations 1-5 above. Accordingly, Equations 7-10 generally summarize the following reactions resulting from the metastable helium.

$$He^* + AB \rightarrow AB^+ + e^- + He \quad (7)$$

$$He^* + AB \rightarrow A + B^+ + e^- + He \quad (8)$$

$$He^* + AB \rightarrow AB^* + He \quad (9)$$

where $AB^* \rightarrow AB + h\gamma$ $$He^* + AB \rightarrow A + B^* + He \quad (10)$$

where $B^* \rightarrow B + h\gamma$

Equations 3, 4, 5, 9 and 10 all describe reactions which form specific and characteristic emission spectra, thereby providing a characteristic signal which enable analysis of the emission source. However, one set of spectra will be emitted after the spark in view of the longer decay times involved, for example, in the last four equations above.

Building on this, a sequence of operation will be described. This involves pulsing the high voltage supply to obtain the appropriate high speed pulse so that certain phenomena occur during the spark, and other phenomena occur after the spark, enabling analysis of different emission spectra at different times relative to the spark and its duration. Discussion of these timing factors can also be tied to a discussion of scaling factors relating to particular voltages.

Measurement of a particular charge species is normally made upstream of the spark gap 30 where the electrometer is located. Carrier gas flow from left to right at a specified rate is a scale factor which relates to system sensitivity. Moreover, system sensitivity is controlled by adjustment of the B+ voltage (positive or negative) applied to the chamber 20. Also, sensitivity is impacted by the choice of the particular electrode 26 and the spacing from the spark gap. Timing is another important scale factor which is exemplified in FIG. 3 in the delay 52 which occurs after the pulse 48 but before enabling the B+ with the wave form 50. Consider typical example. When detecting ions larger than electrons, the detection pulse is applied for a longer interval of time to detect ionic dispersion from the spark gap. Thus, the compound AB forms ionic particles in the spark gap 30 which are measured by periodically pulsing the B+ for detection. Assume that a pulse 44 of twenty microseconds in width causes firing, the spark being the pulse 48 which has a width of substantially less than one microsecond, perhaps a width in the range of 10 to 200 picoseconds. The time delay 52 can be anywhere from 20 to 200 microseconds which enables ions to form after the spark and migrate to the left in FIG. 1 so that the charged particles (less mobile than electrons) are in the vicinity of the appropriate electrodes. This movement is influenced by the geometry and voltage of the several electrodes. In this example, the electrode 27 is controlled by the timer 16 to switch on coextensive with the pulse 50 which is applied to the B+. The electric field formed by the various electrodes 26 controls charged particle dispersion toward the electrode 27. The electrometer 28 measures the impingement of electrons at the terminal 27 and forms an output signal. This can be repeated in cyclical fashion. For instance, the pulse 48 can be repeated with a pulse spacing of one millisecond. In contrast with the flow rate and relative time duration in which a compound AB is in the system, this assures that the peak will be sampled many times. For instance, assume that the GC column eluate discharges the AB compound over a two second interval. Assume further that the next compound is discharged over a four second interval. Assuming the first eluate transit time through the detector 20 is equal to the duration of the peak, over 2,000 samples for that peak will be obtained. The 2,000 data points thus encode the data to assure that proper measurement is obtained and is output for the recorder 41.

As will be observed in the foregoing, the measured charged particles (whether small, highly mobile electrons or larger and less mobile ions) can be timed or gated so that detection of one can occur during the spark and for a very short duration thereafter, or alternately, long after the spark is terminated. Because of the differences that result during the spark versus the reactions occurring after the spark, the phenomena represented by Equations 1-10 above are different and can be distinguished by observation either of the concentration of electrons or ionized particles or by observation of the different emission spectra. Moreover, the emission spectra is different from different regions within the detector. If, for instance, the emission spectra is observed during the spark in the spark gap, the spectra is different from the spectra observed away from the spark gap, as for example, observation of the spectra upstream of the spark gap.

One valuable benefit of the present apparatus is use of the pulsed high voltage spark discharge as a ionization detector devoid of radioactive sources. This can be done either by using the ionization during the discharge or the ionization after the discharge resulting from the metastable helium atoms. The different ionization initiated responses are thus quite different, and they can be used as a qualitative test of suspected compounds. So to speak, the pulsed system serves as two separate detectors testing the carrier and compound AB repetitively, providing two output signals which can be separated and yet which correlate to enhance peak analysis.

If desired, the pulsed high voltage spark discharge system can be used in an electron capture detector devoid of a radioactive source. The helium gas can be provided with a dopant gas; the preferred dopant is $N_2$ which creates a relatively high standing current as a result of ionization of the $N_2$. In the event the eluted molecule tends to capture electrons, the standing current flow through the device will decrease in proportion to eluted molecules introduced into the chamber. Regarding carrier gas choice, the well known inert gases are normally preferred. In some instances, $N_2$ is a good choice.

Connected upstream and downstream, devices are important in use of the detector. For instance, in a manufacturing plant, a single compound AB can be tested repetitively. A variety of unknown compounds can be tested with GC separation as mentioned. The present detector can be connected by any suitable supply system to enable testing and quantification of one or more compounds. The detector output is alternately furnished by the current flow from the electrode 27, or is optically determined by the spectrum analyzer. In both instances, the data is potentially different during the pulse and immediately thereafter in contrast with waiting a long interval after the spark. This enables an entirely different measurement to be obtained.

GC SAMPLE TESTING APPARATUS

Figure 4:
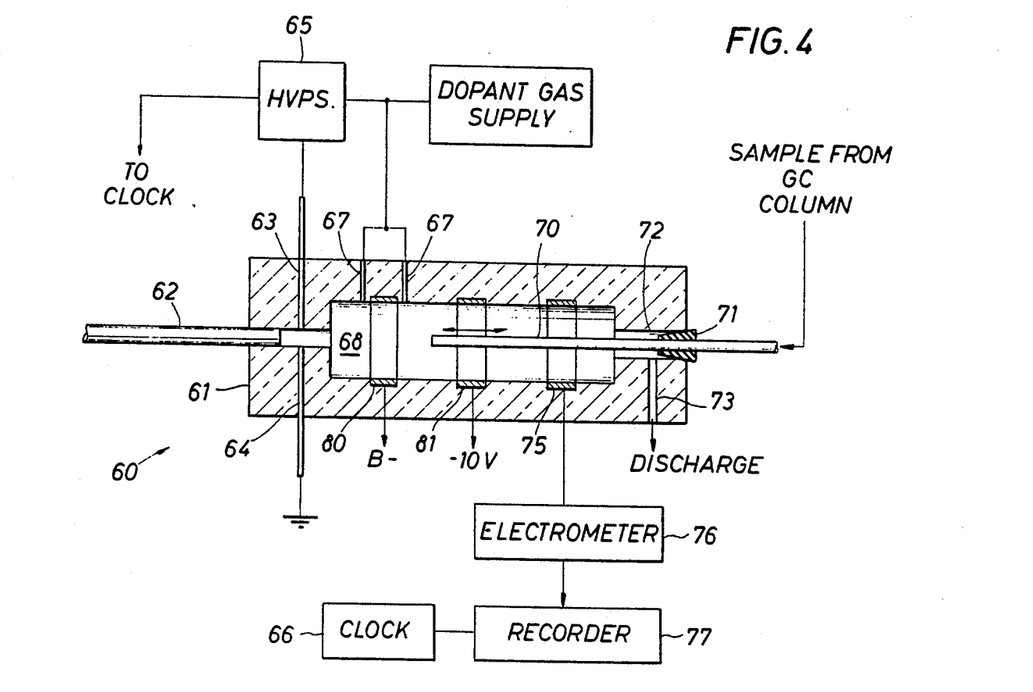
FIG. 4 shows an alternate embodiment of a spark gap system utilizing a downstream addition of a dopant gas from a dopant gas source and a peak separated sample provided from a GC column.

In FIG. 4 of the drawings, the numeral 60 identifies a modified apparatus in accordance with the teachings of the present disclosure. Two modes of use will be described for it. Beginning however with the description of the apparatus, the numeral 61 identifies an elongate cylindrical housing which has an internal flow chamber. On the interior, there are various electrodes and gas flow conduits which will be described. Helium gas is introduced through a flow line 62. Gas flow generally is from left to right as viewed in FIG. 4 of the drawings. The gas flow is primarily helium of high purity. The helium is introduced at a rate which will be described and flows through the spark gap which is provided by the electrodes 63 and 64. They operate in the same fashion as the electrodes shown in FIG. 1 of the drawings. One of the electrodes is grounded and the other electrode is connected with a high voltage power supply (HVPS) 65. The power supply is switched on by a clock 66. The HVPS 65 is pulsed by power so that the clock 66 triggers operation of the high voltage power supply 65. The HVPS 65 provides current flow which is a pulsed DC current flow. It is in the form of pulses. The pulses are relatively short. Ringing might occur but it is preferably reduced substantially by means believed to be well known. The pulse applied to the spark gap is relatively brief as mentioned, typical ranges being less than 1 microsecond up to longer than 1 microsecond, but perhaps less than 50 microseconds. As a generalization, once the DC pulse is formed, the pulse length is not overly significant.

Continuing with FIG. 4 of the drawings, there is an additional gas flow conduit 67. It is shown at two alternate locations. It can be moved relatively over the length of the chamber 68. The chamber 68 is elongate, cylindrical in shape, and has internally constructed metal electrodes. In the chamber, the electrodes have the form of metal rings which are connected with conductors extending through the wall of the housing. The chamber or housing 61 is preferably constructed of an insulative material. For instance, a plastic material will suffice. In other regards, the chamber 68 is sized so that the gap between the electrodes 63 and 64 is in accordance with the gap construction mentioned for the embodiment 20 shown in FIG. 1 of the drawings. Furthermore the scale is sized so that the gas flow through the chamber is perhaps 20 to 30 cubic centimeters of helium per minute in a representative size structure. The dopant introduced through the conduit 67 is introduced at a reduced rate. A typical dopant can be nitrogen, but others are also acceptable. The dopant gas is introduced at a reduced rate in comparison with the helium flow rate. The ratio of dopant to helium gas is typically in the range of 1 part of dopant to 1,000 parts of helium ranging up to 0.1 part per million. This range will encompass most acceptable relative concentrations. There are reasons for deviating from this range but they are not normally encountered. The dopant conduit is at the left hand end while the detector electrode to be described is toward the right hand end of the chamber 68. The flow is from left to right as mentioned; the dopant gas is not introduced at the spark gap but it is introduced upstream of the detection terminal.

There is another gas flow provided into the chamber. The discharge from the GC column is introduced through a movably mounted tube 70. The tube is introduced into the chamber 68 and terminates at a point or location which is selected to adjust sensitivity. The point or tip at which the sample eluate is introduced can vary the sensitivity of the system. For instance, if it is introduced at the very right hand end of the chamber 68, the system is substantially non-operative because it would be significantly downstream of the detector electrode. This would result in introduction of the sample at a location where the sample would be swept from the chamber 68 without engaging the helium metastables in the vicinity of the electrodes and without being subjected to the electric fields which are created around the electrodes interacting with the various gas constituents in the chamber 68.

The tube 70 is adjustable in location and is temporarily held in position or in place by a plug 71. In operation, the tube 70 is first positioned and then the plug is positioned later to assure that the tube is held in a fixed position. Moreover as the tube is moved toward the left, sensitivity is changed as will be detailed below so that movement of the tube 70 is a helpful preliminary step in setting up the apparatus for operation.

The housing 61 is drilled with a concentric passage 72. This is an outlet passage which connects with an outlet tube 73. The tube 73 discharges all of the gases which are introduced into the chamber 68. This discharge passage enables the fluid flow in the chamber 68 to extend from the left to the right and out of the chamber 68 as mentioned.

Going further with this description, the numeral 75 identifies an electrometer electrode which is used for measurements. It is connected to an electrometer 76 and in turn that is connected to a recorder 77. The recorder records the data as a function of time and is therefore connected with the clock 66. The system also includes an additional electrode 80 which is connected with a B+ supply. Another electrode 81 is also included and is connected with another voltage source which in a representative embodiment is −10 volts DC. The function of the electrodes with respect to the operation will be given below.

One mode of use of the present apparatus is as an ionization detector. In that instance, the electrode 81 can be omitted. The electrode 80 is provided with negative voltage. A representative voltage might be −100 volts, extending to perhaps −250 volts. A DC voltage is used for this electrode. In that instance, the structure can be used as an ionization detector. The dopant conduit 67 is deleted for this purpose. The sample from the GC is introduced nearly even with the electrode 80. As a preliminary step, the tube 70 is moved to the left so that it is approximately even with the electrode 80 at the point of sample introduction. This device in operation has helium gas introduced through the spark gap, then sparks are formed as described with respect to FIG. 1, and the sample from the GC source is introduced at a point approximately even with the electrode 80.

The structure shown in FIG. 4 can be used in different fashions. Primarily, the differences relate to the voltages which are placed on the electrode 80. The electrode 80 can be made positive or negative. The system thus can be used as an electron capture detector by using all of the illustrated electrodes 75, 80 and 81. Alternately, it can be used in a different fashion simply by disconnecting the electrode 81, or optionally by removing the electrode 81. Thus the operation of the device becomes variable dependent on the interplay of several important factors. One important factor is the position of the tip of the GC sample tube 70. It is inserted from the right to the left by a desired distance. As that distance is varied, sensitivity of the system is also varied. Another important factor is the choice of positive or negative voltage on the terminal 80. This terminal or electrode has an influence on the flow of metastable helium moving from left to right which interacts with the introduced gaseous sample from the line 70. Another factor is the voltage placed on the electrode 81. Finally, the presence or absence of a dopant gas inserted through the line 67 should be noted. As a generalization, it provides even further variation in system operation.

The detector 60 of FIG. 4 is usually operated at ambient temperature, or it can be opearted at raised temperatures of up to 300° C. The pressure within the chamber is substantially equal to room pressure. The helium flow through the line 62 typically is in the range of about 20 to 30 cubic centimeters per minute. As mentioned, ratios were given for the dopant gas which is added optionally as mentioned. Finally, another scale factor which is varied is the duty cycle of the HVPS 65, and it is varied in accordance with any suitable sequence. An example was given with regard to FIG. 3 of the drawings. In that instance, the pulse 48 is formed after charging of the HVPS 65 at which time discharge occurs and the spark across the gap is then triggered. The spark is the source of the metastable helium which decays over an interval to provide the necessary energy for interaction with sample molecules and subsequent detection at the electrometer electrode.

IMPROVED OPTICAL MEASURING SYSTEM

Figure 5:
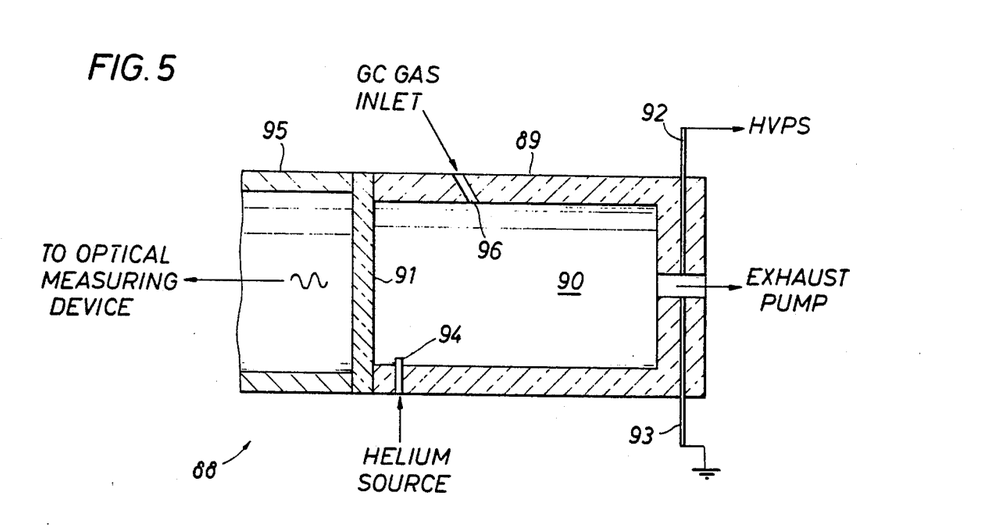
FIG. 5 shows an alternative construction of a chamber providing spectral emission.

Attention is momentarily directed to FIG. 5 of the drawings where the numeral 88 identifies an alternate construction of measuring apparatus which provides an optical output. The construction of the device will be described first and the mode of operation will then be given. In FIG. 5, the numeral 89 identifies a cylindrical shell or housing. It defines an internal mixing chamber 90. The housing is formed of a material which is opaque to light emissions. It does however have a single window at 91. The window is formed of an appropriate material to pass a wave length of interest. The wave length of interest is selected for a region of investigation. As known, the visible light spectrum is approximately 4,000 to 7,000 Å, and that frequency range can be selected. There are other reasons to select other frequency ranges, and frequency ranges which are outside the visible spetrum can also be chosen. Appropriate for the frequency range, a particular material is chosen for the window 91 so that it is essentially transparent to that particular frequency range. The numerals 92 and 93 identify the electrodes of the present disclosure which are similar to those shown in FIGS. 1 and 2. The DC spark in accordance with the teachings of this disclosure is applied periodically to the electrodes as mentioned. They are constructed with ends adjacent to the hole in the structure which connects with an outlet passage and then delivers the outlet gas flow to an exhaust pump. The pump continually clears the chamber. The flow out of the chamber 90 is approximately equal to the flow into the chamber 90. There is no particular gain by operating the chamber 90 at an elevated pressure. An inlet passage is identified at 94. It delivers helium from a suitable helium source into the chamber 90. It sweeps over the surface of the window 91, that window being formed of a transparent material as mentioned. The preferred carrier gas is helium. It is an inert gas in practically every circumstance. It is introduced in a region where it flows adjacent to or over the window 91. In that region, the window is therefore protected by the gas in this region. This reduces accumulation of a film on the window which might otherwise reduce optical transmission through the window. The window 91 is adjacent to a vacuum chamber 95. The vacuum chamber 95 is a region of reduced air content. As a generalization, air (meaning primarily nitrogen and oxygen) is an absorbent medium with reduced optical transmission, especially to selected frequencies. The vacuum chamber enables optical transmission of light emitted from the spark to an optical measuring device. It is believed that optical measuring devices of the appropriate type and nature are well known.

A sample of interest is introduced through a GC system and delivered into the chamber 90 through an inlet 96. The GC gas sample mixes with the helium in the chamber 90. The ratio of the sample to the helium is a scale factor which is determined by the flow rates of the sample and the helium. It is also determined in part by the volume of the chamber 90. Suffice it to say, these are scale factors which can be modified to achieve a particular ratio on mixing the sample with the helium gas.

The inlet 96 is at an angle to direct the sample flow away from the window 91. It is assumed that the sample as introduced typically does not impact the material forming the window 91. It can be any type of chemical or biological sample being analyzed. In the state in which it is received from the GC separation system, the sample typically is simply mixed with the helium in the chamber. The sample from the GC source and the helium in the mixed condition flow out of the chamber 90 and are forced to flow through the spark chamber. On flowing through that spark, the electrical spark interacts with the helium and sample to provide optical emissions. They are normally scattered in all directions. Of particular importance to the present apparatus, the optical emissions are directed toward the window 91 and are transmitted through the window. The window is able to transmit the optical emissions to the optical measuring device on the opposite side of the window. This is accomplished in the desired fashion so that the optical measuring instrument can observe the emissions and make the necessary measurements. For instance, one form of measurement is detection of the frequency or wave length of particular emissions, and another type of measurement is the duration and intensity of such emissions. These measurements typically are made by the optical measuring instrument on transmission through the window 91. The window 91 is protected from chemical damage. It is not uncommon that the window surface exposed to the chamber 90 will either become etched or at least smudged with materials derived from the sample in the chamber 90 especially after the sample is highly energized on encountering the spark. In this particular instance, the embodiment 88 is configured so that the GC sample is removed from the chamber rather quickly and the exhaustion of the highly activated sample material protects the window 91. It is not uncommon to require daily cleaning of the window in systems where the window is in contact with the sample after it has been energized in the spark. For instance, windows are normally installed for easy removal so that they can either be washed or otherwise cleaned for the purpose of clearing the window of any film or smudge which might obscure optical transmission. Suffice it to say, this type arrangement is protective of the window and enables the equipment to operate with better optical transmission for longer intervals.

In the embodiment of FIG. 5, in the spark gap between the electrodes 92 and 93, the mixture of helium and sample is exposed to the electrical spark which creates the requisite excited states causing the optical emissions. Fortunately, as a result of the geometry of this construction, the highly energized molecules making up the sample migrate out of the chamber, not back toward the window 91. The gas flow patterns in the chamber are away from the window and not toward the window. The possibility of impingement of highly energized molecules on the window is substantially nil because that would require migration out of the spark gap against the gas flow patterns prevailing in the chamber. This protects the window and enables the device to operate for a longer interval.

While the foregoing is directed to the preferred embodiments, the scope thereof is determined by the claims which follow.

What is claimed is:

1. A charged particle detector comprising:
   (a) a closed chamber having a carrier gas flow inlet at a first end and spaced outlet at a second end to enable gas flow therethrough;
   (b) spaced electrodes forming a spark responsive to DC current flow sufficient to enable an electrical spark to be formed between said electrodes locating the spark thereacross, said electrodes being positioned to form a spark in carrier gas flow into said chamber and create charged particles;
   (c) a spaced detector electrode in said chamber for collection of charged particles downstream of the spark across the gap wherein the charged particles move toward said detector electrode to enable a current to be formed indicative of charged particle concentration in said chamber; and
   (d) an inlet into said chamber for controllably introducing a sample gas flow from a GC source downstream from said spark forming electrodes so that said sample gas flow and said carrier gas flow provide charged particles for said detector electrode.

2. The apparatus of claim 1 wherein the sample is diffused with charged carrier gas molecules in said chamber.

3. The apparatus of claim 1 wherein said carrier gas comprises helium atoms having an excited high energy metastable state which transition to a lower energy state, and thereby interact with the sample from the GC source.

4. The apparatus of claim 1 wherein said detector electrode is spaced downstream from said spark forming electrodes, and at least one electrode is positioned therebetween connected to a voltage source to control charged particle impingement thereon.

5. The apparatus of claim 4 including multiple electrodes connected to different voltage levels.

6. The apparatus of claim 1 wherein said spark forming electrodes are periodically pulsed with DC current to form a DC spark during pulsing wherein the spark forms an incandescent current flow across said gap, and said spark electrodes are flush mounted in a surrounding circular ring of non-conductive material to direct gas flow through the spark.

7. The apparatus of claim 6 wherein the spark forming electrodes are aligned conductors having ends facing across said gap, and said conductors are sufficiently small that spark discharge across the gap is from end to end.

8. The apparatus of claim 1 wherein said chamber is cylindrical and said carrier gas is introduced at one end thereof and said electrode comprises a circular electrode downstream in said chamber.

9. The apparatus of claim 1 wherein said GC source inlet is located downstream of said carrier gas inlet to said chamber so that said sample is not input to said spark gap.

10. A method of analyzing a sample compound comprising the steps of:
(a) flowing a carrier gas through a chamber;
(b) exposing the carrier gas to a repetitive DC current spark;
(c) forming energized particles as a result of the spark through the gas;
(d) introducing a gaseous sample into the chamber;
(e) mixing the energized particles with the gaseous sample, and dispersing the energized particles into the gaseous sample;
(f) measuring a characteristic of the energy state of the gaseous sample; and
(g) wherein the measurement step occurs after mixing the gaseous sample with energized particles of the carrier gas.

11. The method of claim 10 wherein the carrier gas is an inert gas capable of being changed to a metastable state by the spark, and further sustains the metastable state for a controlled time interval after the spark.

12. The method of claim 11 wherein the carrier gas is helium and forms metastable helium; and further wherein the gaseous sample provides charged particles for measurement.

13. A gas detector for identification and quantification of sample compounds, comprising:
(a) an elongate chamber having a chamber inlet at one end and an outlet at the other end, and a gas flow path between said inlet and outlet ends;
(b) means for flowing carrier gas through said chamber between said inlet and outlet ends;
(c) two electrodes spaced apart and located at said inlet to produce short repeated high voltage DC current sparks across said gas flow path and wherein spark duration minimizes electrode erosion while forming energized particles in the chamber; and
(d) means for introducing sample gas into said chamber; and
(e) means responsive to the energy states of the interacted sample gas and charged particles of the carrier gas from to enable detection in said chamber.

14. The apparatus of claim 13 wherein a potential gradient is created at a collector electrode in said chamber for the measurement of sample gas ionization.

15. The apparatus of claim 13 wherein a potential gradient is created at a collector electrode in said chamber for sample gas electron capture phenomena.

16. The apparatus of claim 15 wherein a dopant is added into the chamber by a dopant supply means to provide a source of thermalized electrons to measure electron capture.

17. A gas detector for identification and quantitation of sample compounds, comprising:
(a) an elongated chamber having a chamber inlet at one end and an outlet at the other end, and a gas flow path between said inlet and outlet ends;
(b) means for flowing carrier gas through said chamber;
(c) moveable means for introducing sample gas into said chamber at a varied location;
(d) two electrodes spaced apart and located to produce short repeated high voltage DC current sparks within said chamber and across said carrier gas flow path and wherein spark duration minimizes electrode erosion; and
(e) wherein ions are produced by the spark or by excited metastable species of the carrier gas.

18. The apparatus of claim 17 wherein a potential gradient is created at a collector electrode in said chamber for the measurement of ionization or electron capture phenomena.

19. The apparatus of claim 17 wherein dopant is added to the chamber to provide a source of thermalized electrons to measure electron capture.

20. The apparatus of claim 17 wherein said moveable means includes a tube having an end moveable between said inlet and outlet ends to a location enabling charging of the response to carrier gas interaction with the spark.

21. Detecting apparatus comprising:
(a) an elongate chamber having an inlet at one end and an outlet at its other end, and a carrier gas flow path between said inlet and outlet;
(b) spaced discharge electrodes disposed within said chamber to form an electrical discharge gap between such electrodes in said gas flow path of said chamber;
(c) means for flowing a sample gas into said chamber without flowing through said electrodes;
(d) means for repetitively applying electrical discharges across said discharge gap of said spaced electrodes in the path of a carrier gas thereby changing the atomic state of said carrier gas; and
(e) means for measuring a characteristic of the charged atomic state of said sample gas.

22. The apparatus of claim 21 wherein said electrical discharges are of a duration of up to about 50 microseconds in length with a time period between pulses of up to about 500 microseconds.

23. A method of measuring a characteristic of a gas sample comprising the steps of:
(a) providing an elongate chamber having an inlet at one end and an outlet at its other end and a gas flow path between said inlet and outlet, and having spaced discharge electrodes disposed within said chamber to form an electrical discharge gap between such electrodes in said gas flow path of said chamber;
(b) flowing a carrier gas first through said electrical discharge and along said gas flow path of said chamber;
(c) repetitively applying electrical discharges across said discharge gap in the path of said carrier gas thereby changing the energy state of said carrier gas;

(d) introducing a sample gas into the chamber downstream of said spark forming electrodes; and
(e) measuring a characteristic of the energy state of said sample gas.

24. The method of claim 23 wherein said measuring step comprises the steps of providing a charge collecting electrode within said chamber which is longitudinally spaced from said discharge electrodes of said chamber, providing an electric field within said chamber for attracting electrons produced in said chamber as a result of said electrical discharges passing through said carrier gas, measuring charge attracted to said charge collecting electrode substantially during the time of said periodic electrical discharges and indicating the measured current, measuring charge attracted to said charge collecting electrode during the time between said period electrical discharges and indicating the measured current, as an indicator of a characteristic of said sample gas.

25. An apparatus for measuring the optical emissions unique to a sample comprising:
(a) chamber means having an optically transparent window at a first end of said chamber means for enabling light to pass through said window;
(b) inlet means directing a flow of an inert gas into said chamber means wherein the flow sweeps over a region adjacent to said window;
(c) an outlet from said chamber at a second end of said chamber means;
(d) spark forming means in said chamber located so that a spark formed thereby forms light emitted by the spark, and the light is directed toward said window; and
(e) means for introducing a gas sample into said chamber means to enable said sample to be introduced into the spark and thereby form light characteristic of said sample so that light passing through said window characteristically represents the sample, wherein said means for introducing a gas sample is downstream of said inert gas inlet means.

* * * * *